US011911544B2

(12) United States Patent
Furuhashi et al.

(10) Patent No.: US 11,911,544 B2
(45) Date of Patent: Feb. 27, 2024

(54) BLOOD PURIFICATION APPARATUS (71) Applicant: Nikkiso Company Limited, Tokyo (JP)

(72) Inventors: Tomohiro Furuhashi, Shizuoka (JP); Yuki Eda, Shizuoka (JP); Masaaki Ohta, Shizuoka (JP); Kenji Furuhashi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 405 days.

(21) Appl. No.: 17/225,604

(22) Filed: Apr. 8, 2021

(65) Prior Publication Data

US 2021/0220537 A1    Jul. 22, 2021

Related U.S. Application Data

(63) Continuation of application No. PCT/JP2019/043766, filed on Nov. 7, 2019.

(30) Foreign Application Priority Data

Nov. 8, 2018  (JP) .............................. 2018-210893

(51) Int. Cl.
*A61M 1/16* (2006.01)
*A61M 1/34* (2006.01)

(52) U.S. Cl.
CPC ............ *A61M 1/1601* (2014.02); *A61M 1/16* (2013.01); *A61M 1/1654* (2013.01); *A61M 1/34* (2013.01);
(Continued)

(58) Field of Classification Search
CPC .... A61M 1/16; A61M 1/1601; A61M 1/1654; A61M 1/34; A61M 1/3413;
(Continued)

(56) References Cited

U.S. PATENT DOCUMENTS

2010/0087771 A1   4/2010  Karakama et al.
2018/0193544 A1   7/2018  Pouchoulin

FOREIGN PATENT DOCUMENTS

DE        4122171 A1    1/1993
JP    S56-036963 A      4/1981
(Continued)

OTHER PUBLICATIONS

European Search Report for Application No. 19882918.6, dated Jun. 1, 2022, 16 pgs.
(Continued)

*Primary Examiner* — John Kim
(74) *Attorney, Agent, or Firm* — Young Basile Hanlon & MacFarlane, P.C.

(57) ABSTRACT

A blood purification apparatus that includes a blood circuit including an arterial blood circuit and a venous blood circuit and that allows a patient's blood to extracorporeally circulate, with a blood purifier that is interposed between the arterial blood circuit and the venous blood circuit and purifies; a dialysate temporary chamber that temporarily stores dialysate received from a dialysate storage supported by a supporting unit; a substitution-fluid temporary chamber that temporarily stores substitution fluid received from a substitution-fluid storage supported by the supporting unit; a first dialysate introduction line through which the dialysate in the dialysate storage flows into the dialysate temporary chamber; and a substitution line through which the substitution fluid in the substitution-fluid storage flows into the substitution-fluid temporary chamber. The blood purification apparatus includes a dialysate transfer pump provided to the first dialysate introduction line and that transfers the dialysate in the dialysate storage to the dialysate temporary chamber, a substitution-fluid transfer pump provided to the substitution line and that transfers the substitution fluid in the substitution-fluid storage to the substitution-fluid tem-
(Continued)

porary chamber, and a control unit that controls the dialysate transfer pump and the substitution-fluid transfer pump.

11 Claims, 8 Drawing Sheets

(52) U.S. Cl.
CPC ........ *A61M 1/3413* (2013.01); *A61M 1/3434* (2014.02); *A61M 1/3441* (2013.01); *A61M 2205/3334* (2013.01); *A61M 2205/3382* (2013.01); *A61M 2205/3393* (2013.01); *A61M 2209/084* (2013.01)

(58) Field of Classification Search
CPC .............. A61M 1/3434; A61M 1/3441; A61M 2205/3334; A61M 2205/3382; A61M 2205/3393; A61M 2209/084
See application file for complete search history.

(56) References Cited

FOREIGN PATENT DOCUMENTS

| | | |
|---|---|---|
| JP | 2006-095184 A | 4/2006 |
| JP | 2012-200275 A | 10/2012 |
| WO | 2004/014463 A1 | 2/2004 |
| WO | 2016-104720 A1 | 6/2016 |

OTHER PUBLICATIONS

Potentially related Patent application filed Apr. 8, 2021, entitled "Blood Purification Apparatus", published as WO2020096018A1.

BLOOD PURIFICATION APPARATUS

CROSS-REFERENCE TO RELATED APPLICATION(S)

This application is a continuation of International Application No. PCT/JP2019/043766, filed on Nov. 7, 2019, which claims priority to Japanese Application No. 2018-210893, filed on Nov. 8, 2018, the entire disclosures of which are hereby incorporated by reference.

FIELD

The present teachings relate to a blood purification apparatus for purifying blood of a patient while causing the blood to extracorporeally circulate.

BACKGROUND

In general, a blood purification apparatus for giving dialysis treatment includes an arterial blood circuit and a venous blood circuit that form a blood circuit for causing blood of a patient to extracorporeally circulate, a blood purifier for purifying the blood extracorporeally circulating through the blood circuit, and an apparatus body provided with various treatment devices, such as a blood pump, for performing blood purification treatment with the blood circuit and the blood purifier. The arterial blood circuit and the venous blood circuit are each provided with a vascular access catheter or a puncture needle (an arterial puncture needle or a venous puncture needle) that is attachable to a distal end thereof.

For example, after the patient is punctured with the arterial puncture needle and the venous puncture needle, the blood pump is activated. Thus, blood of the patient flows through the arterial blood circuit and the venous blood circuit. In this flowing process, the blood is purified by the blood purifier. In dialysis treatment, a dialysate introduction line for introducing dialysate into the blood purifier and a drain-liquid drain line for draining drain liquid from the blood purifier are connected to the blood purifier.

Methods established for blood purification treatment include hemodialysis (HD) in which dialysate is made to flow through dialysate flow routes provided in the blood purifier and substances in the blood are removed by the effect of diffusion through blood purification membranes, hemofiltration (HF) in which water and substances in the blood are removed by the effect of ultrafiltration pressure generated in the blood purifier and an amount of substitution fluid that is equal to the amount of water removed is infused into the blood, and hemodiafiltration (HDF) in which hemodialysis (HD) and hemofiltration (HF) are performed simultaneously. In particular, when blood purification treatment is given to a patient having a disease such as acute renal failure, the treatment method needs to be switched among hemodialysis (HD), hemofiltration (HF), and hemodiafiltration (HDF) during a series of treatment steps in accordance with the patient's condition.

To meet the above demand, a blood purification apparatus according to a known proposal includes a dialysate bag storing a predetermined amount of dialysate and a substitution-fluid bag storing a predetermined amount of substitution fluid that are supported at predetermined height positions, a dialysate temporary chamber that stores the dialysate received from the dialysate bag, and a substitution-fluid temporary chamber that stores the substitution fluid received from the substitution-fluid bag. The dialysate and the substitution fluid stored in the respective temporary chambers are introduced into a blood purifier and into a blood circuit.

The dialysate bag and the substitution-fluid bag are positioned higher than the dialysate temporary chamber and the substitution-fluid temporary chamber, respectively. When the dialysate temporary chamber or the substitution-fluid temporary chamber becomes empty, the dialysate in the dialysate bag or the substitution fluid in the substitution-fluid bag flows into and is stored in the dialysate temporary chamber or the substitution-fluid temporary chamber because of the height-position difference (the height-position difference between the bag and the temporary chamber). Such a technique is not disclosed by any publicly available patent literature. Therefore, no patent literature is cited herein.

SUMMARY

In the above known blood purification apparatus, the dialysate and the substitution fluid in the dialysate bag (dialysate storage) and the substitution-fluid bag (substitution-fluid storage) are each made to flow into and be stored in a corresponding one of the dialysate temporary chamber and the substitution-fluid temporary chamber by utilizing the height-position difference between the bag and the temporary chamber. Therefore, the dialysate storage and the substitution-fluid storage need to be supported at satisfactorily high positions. Such a situation leads to a problem that the positions (arrangement) of supporting the dialysate storage and the substitution-fluid storage are limited, reducing the degree of freedom in the layout of the dialysate storage and the substitution-fluid storage.

The present teachings have been conceived in view of the above circumstances and provides a blood purification apparatus in which liquid transfer from the dialysate storage and the substitution-fluid storage to the dialysate temporary chamber and the substitution-fluid temporary chamber is achieved in a good manner, with an increased degree of freedom in the layout of the dialysate storage and the substitution-fluid storage.

Variation 1 may comprise: a blood purification apparatus that includes a blood circuit including an arterial blood circuit and a venous blood circuit and that allows a patient's blood to extracorporeally circulate, with a blood purifier that is interposed between the arterial blood circuit and the venous blood circuit and purifies the patient's blood; a dialysate temporary chamber that temporarily stores dialysate received from a dialysate storage supported by a supporting unit; a substitution-fluid temporary chamber that temporarily stores substitution fluid received from a substitution-fluid storage supported by the supporting unit; a first dialysate introduction line through which the dialysate in the dialysate storage flows into the dialysate temporary chamber; and a substitution line through which the substitution fluid in the substitution-fluid storage flows into the substitution-fluid temporary chamber. The blood purification apparatus includes a dialysate transfer pump provided to the first dialysate introduction line and that transfers the dialysate in the dialysate storage to the dialysate temporary chamber; a substitution-fluid transfer pump provided to the substitution line and that transfers the substitution fluid in the substitution-fluid storage to the substitution-fluid temporary chamber; and a control unit that controls the dialysate transfer pump and the substitution-fluid transfer pump.

Variation 2 may comprise, the blood purification apparatus according to variation 1 further includes a drain-liquid temporary chamber that stores drain liquid received from the blood purifier, a drain-liquid drain line through which the drain liquid in the drain-liquid temporary chamber is drained to an outside of the apparatus, and a drain-liquid transfer pump provided to the drain-liquid drain line and that transfers the drain liquid in the drain-liquid temporary chamber to the outside of the apparatus. Furthermore, the control unit controls the drain-liquid transfer pump in addition to the dialysate transfer pump and the substitution-fluid transfer pump.

Variation 3 may comprise, the blood purification apparatus according to variation 1 or 2, the dialysate transfer pump, the substitution-fluid transfer pump, and the drain-liquid transfer pump are each a peristaltic pump that delivers liquid by squeezing a flexible tube forming a flow route for a corresponding one of the dialysate, the substitution fluid, and the drain liquid.

Variation 4 may comprise, the blood purification apparatus according to any of variations 1 to 3 further includes a second dialysate introduction line through which the dialysate in the dialysate temporary chamber flows into the blood purifier, and a dialysate introduction pump provided to the second dialysate introduction line and that delivers the dialysate in the dialysate temporary chamber to the blood purifier. Furthermore, the control unit controls a flow rate of the dialysate transfer pump in accordance with a flow rate of the dialysate introduction pump.

Variation 5 may comprise, the blood purification apparatus according to any of variations 1 to 4, a flow rate of the dialysate introduction pump is set to a value greater than 6000 mU/h.

Variation 6 may comprise, the blood purification apparatus according to any of variations 1 to 5, a height-position difference between a bottom of the dialysate storage supported by the supporting unit and a top of the dialysate temporary chamber and a height-position difference between a bottom of the substitution-fluid storage supported by the supporting unit and a top of the substitution-fluid temporary chamber are each smaller than 40 cm.

Variation 7 may comprise, the blood purification apparatus according to any of variations 1 to 6, a height position at bottoms of the dialysate storage and the substitution-fluid storage supported by the supporting unit is lower than 160 cm.

Variation 8 may comprise, the blood purification apparatus according to any of variations 1 to 7, the supporting unit is configured such that a height position where at least one of the dialysate storage and the substitution-fluid storage is supported is adjustable.

Variation 9 may comprise, the blood purification apparatus according to any of variations 1 to 8, reaching of an amount of liquid in the dialysate temporary chamber or the substitution-fluid temporary chamber to a specified value is identified by a total amount of flow generated by the dialysate transfer pump or the substitution-fluid transfer pump.

Variation 10 may comprise, the blood purification apparatus according to any of variations 1 to 9 further includes a detecting unit that detects reaching of an amount of liquid in the dialysate temporary chamber to a specified value. Furthermore, the control unit stops the dialysate transfer pump when the reaching of the amount of liquid in the dialysate temporary chamber to the specified value is detected by the detecting unit.

Variation 11 may comprise, the blood purification apparatus according to any of variations 1 to 10 further includes a detecting unit that detects reaching of an amount of liquid in the substitution temporary chamber to a specified value. Furthermore, the control unit stops the substitution-fluid transfer pump when the reaching of the amount of liquid in the substitution temporary chamber to the specified value is detected by the detecting unit.

Variation 1 may comprise the blood purification apparatus includes the dialysate transfer pump provided to the first dialysate introduction line and that transfers the dialysate in the dialysate storage to the dialysate temporary chamber, the substitution-fluid transfer pump provided to the substitution line and that transfers the substitution fluid in the substitution-fluid storage to the substitution-fluid temporary chamber, and the control unit that controls the dialysate transfer pump and the substitution-fluid transfer pump. Therefore, the transfer from the dialysate storage and the substitution-fluid storage to the dialysate temporary chamber and the substitution-fluid temporary chamber, respectively, can be achieved in a good manner, and the degree of freedom in the layout of the dialysate storage and the substitution-fluid storage can be increased.

Variation 2 may comprise, the blood purification apparatus further includes the drain-liquid temporary chamber that stores drain liquid received from the blood purifier, the drain-liquid drain line through which the drain liquid in the drain-liquid temporary chamber is drained to the outside of the apparatus, and the drain-liquid transfer pump provided to the drain-liquid drain line and that transfers the drain liquid in the drain-liquid temporary chamber to the outside of the apparatus. Furthermore, the control unit controls the drain-liquid transfer pump in addition to the dialysate transfer pump and the substitution-fluid transfer pump. Therefore, no limit is imposed on the height position of the drain-liquid temporary chamber, and the degree of freedom in the layout of the drain-liquid temporary chamber in addition to the degree of freedom in the layout of the dialysate storage and the substitution-fluid storage can be increased.

Variation 3 may comprise, the dialysate transfer pump, the substitution-fluid transfer pump, and the drain-liquid transfer pump are each a peristaltic pump that delivers liquid by squeezing a flexible tube forming a flow route for a corresponding one of the dialysate, the substitution fluid, and the drain liquid. Therefore, the flow route for each of the dialysate, the substitution fluid, and the drain liquid can be closed by stopping the peristaltic pump, with no need to provide any separate clamp unit or the like.

Variation 4 may comprise, the blood purification apparatus further includes the second dialysate introduction line through which the dialysate in the dialysate temporary chamber flows into the blood purifier, and the dialysate introduction pump provided to the second dialysate introduction line and that delivers the dialysate in the dialysate temporary chamber to the blood purifier. Furthermore, the control unit controls the flow rate of the dialysate transfer pump in accordance with the flow rate of the dialysate introduction pump. Therefore, the flow rate of the dialysate to be transferred to the dialysate temporary chamber can be made greater than the flow rate of the dialysate to be introduced from the dialysate temporary chamber into the blood purifier. Consequently, the occurrence of shortage of the dialysate in the dialysate temporary chamber can be avoided assuredly.

Variation 5 may comprise, the flow rate of the dialysate introduction pump is set to a value greater than 6000 mU/h. Therefore, the dialysis efficiency in the blood purification treatment can be increased.

Variation 6 may comprise, the height-position difference between the bottom of the dialysate storage supported by the supporting unit and the top of the dialysate temporary chamber and the height-position difference between the bottom of the substitution-fluid storage supported by the supporting unit and the top of the substitution-fluid temporary chamber are each smaller than 40 cm. Therefore, the ease of work in replacing the dialysate storage and the substitution-fluid storage with new ones can be increased.

Variation 7 may comprise, the height position at the bottoms of the dialysate storage and the substitution-fluid storage supported by the supporting unit is lower than 160 cm. Therefore, the ease of work in replacing the dialysate storage and the substitution-fluid storage with new ones can be increased further.

Variation 8 may comprise, the supporting unit is configured such that the height position where at least one of the dialysate storage and the substitution-fluid storage is supported is adjustable. Therefore, it is easy to support the dialysate storage and the substitution-fluid storage at respective positions corresponding to the layout of the dialysate storage and the substitution-fluid storage.

Variation 9 may comprise, the reaching of the amount of liquid in the dialysate temporary chamber or the substitution-fluid temporary chamber to the specified value is identified by the total amount of flow generated by the dialysate transfer pump or the substitution-fluid transfer pump. Therefore, a situation where the dialysate temporary chamber or the substitution-fluid temporary chamber has become full can be detected without providing liquid-level sensors.

Variation 10 may comprise, the blood purification apparatus further includes the detecting unit that detects the reaching of the amount of liquid in the dialysate temporary chamber to the specified value. Furthermore, the control unit stops the dialysate transfer pump when the reaching of the amount of liquid in the dialysate temporary chamber to the specified value is detected by the detecting unit. Therefore, the supply of the dialysate from the dialysate storage can be achieved in a good manner.

Variation 11 may comprise, the blood purification apparatus further includes the detecting unit that detects the reaching of the amount of liquid in the substitution temporary chamber to the specified value. Furthermore, the control unit stops the substitution-fluid transfer pump when the reaching of the amount of liquid in the substitution temporary chamber to the specified value is detected by the detecting unit. Therefore, the supply of the substitution fluid from the substitution-fluid storage can be achieved in a good manner.

DETAILED DESCRIPTION

Embodiments of the present teachings will now be described specifically with reference to the drawings.

Figure 1:
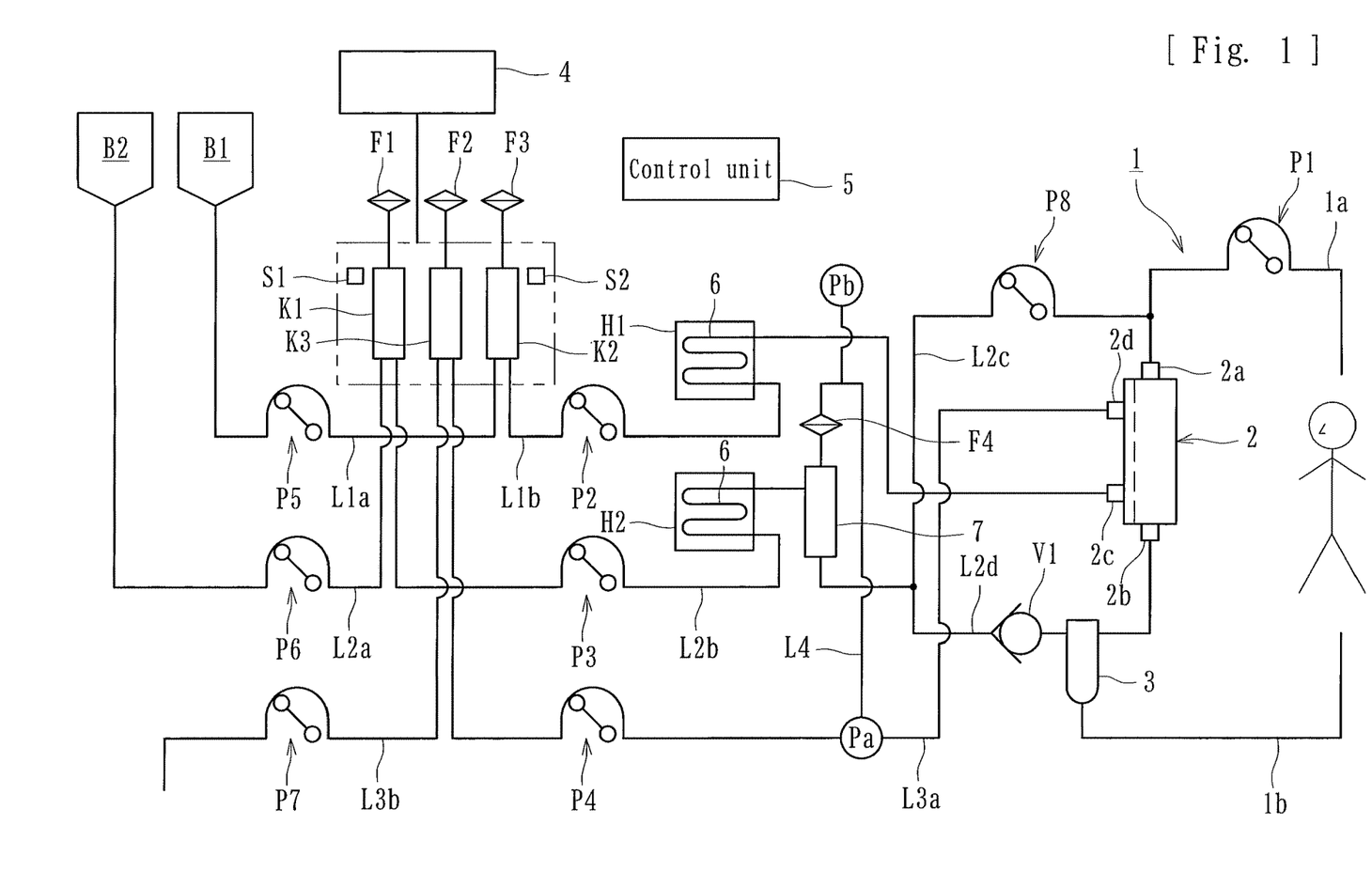
FIG. 1 is a schematic diagram of a blood purification apparatus according to an embodiment of the present invention.
Figure 2:
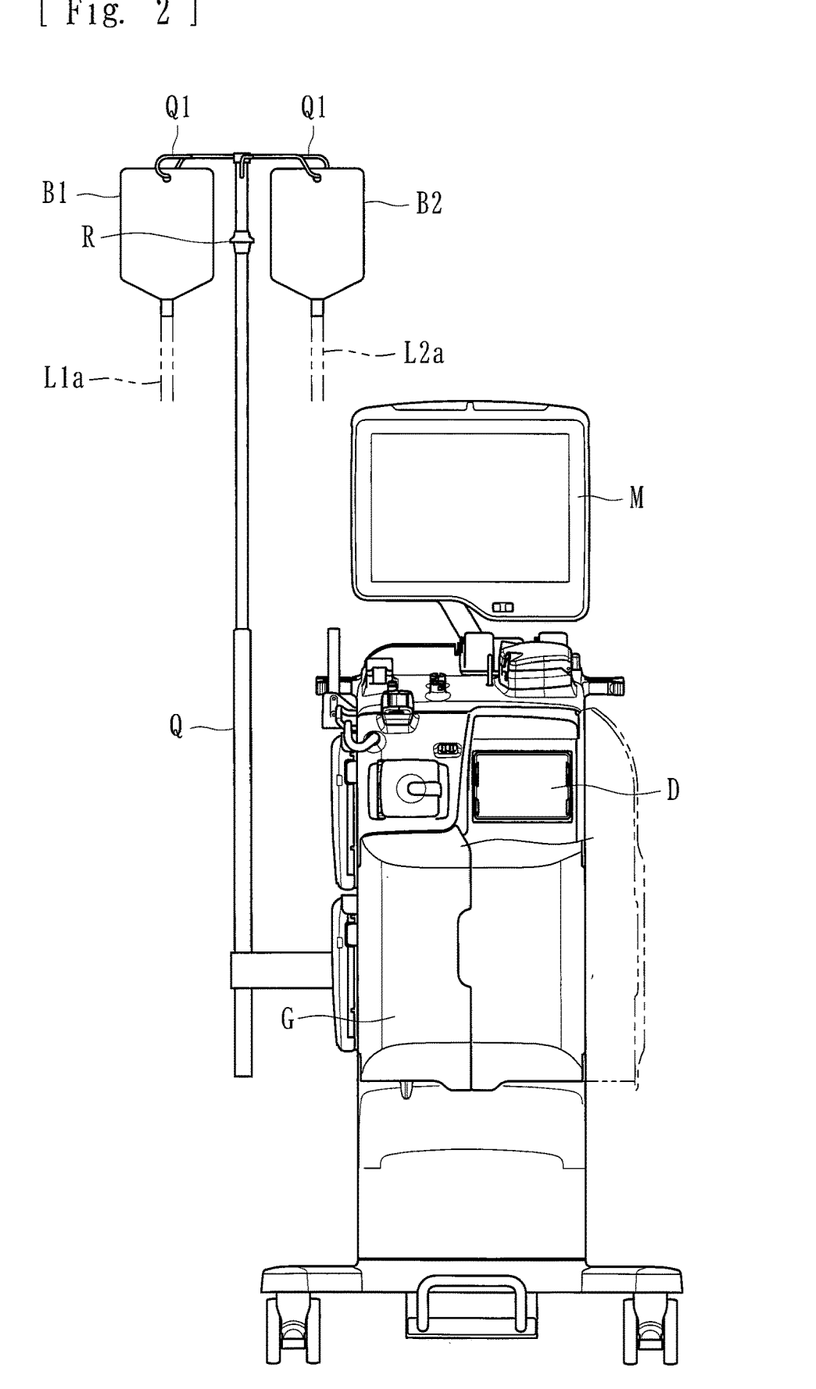
FIG. 2 illustrates the appearance of the blood purification apparatus in front view (with temporary chambers yet to be attached).
Figure 3:
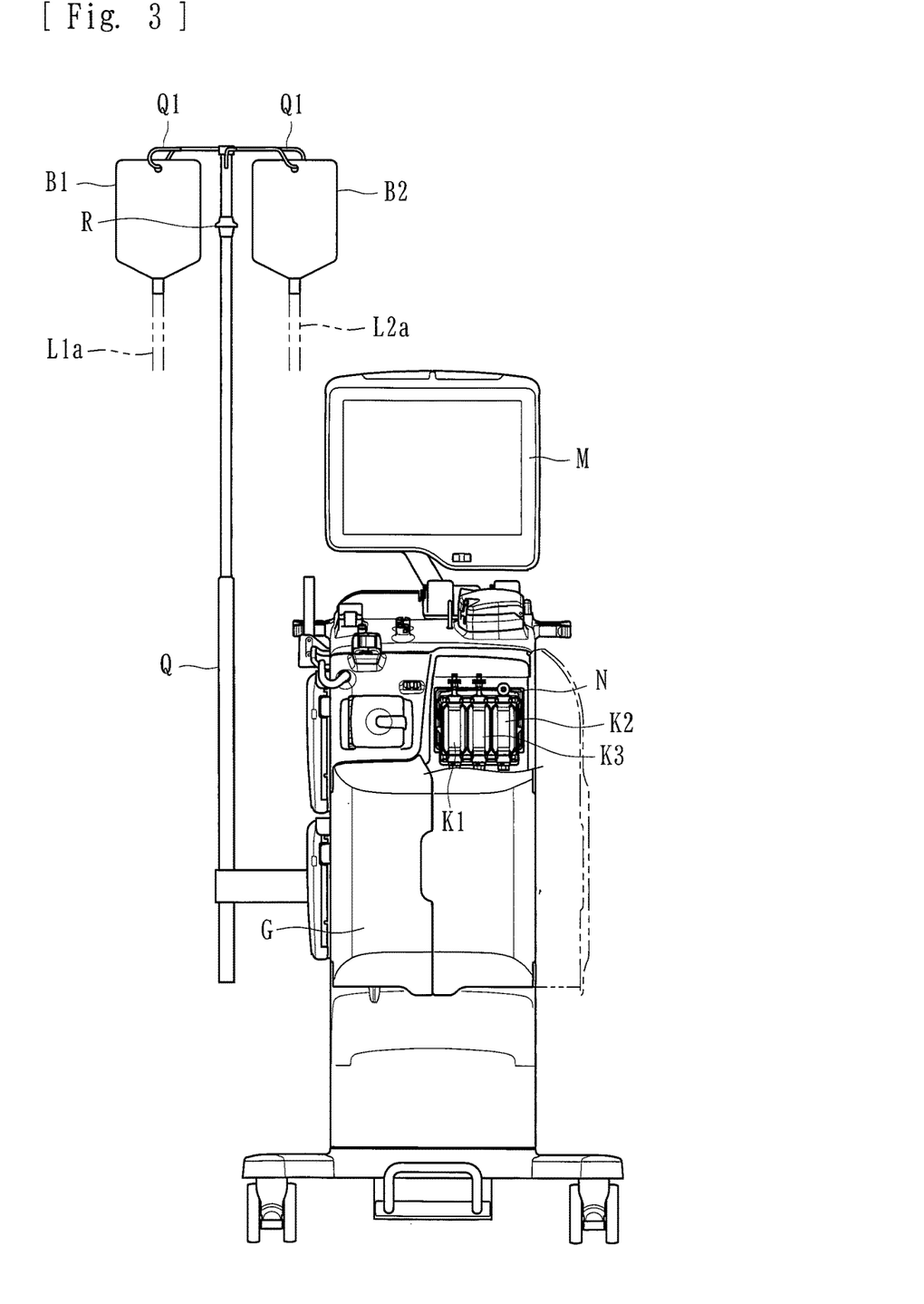
FIG. 3 illustrates the appearance of the blood purification apparatus in front view (with the temporary chambers attached).

A blood purification apparatus according to an embodiment is applied to a hemodialysis apparatus for purifying blood of a patient while causing the blood to extracorporeally circulate. As illustrated in FIGS. 1 to 3, the apparatus includes a blood circuit 1 including an arterial blood circuit 1a and a venous blood circuit 1b; a dialyzer 2 (a blood purifier) provided between the arterial blood circuit 1a and the venous blood circuit 1b and that purifies blood flowing through the blood circuit 1; a first dialysate introduction line L1a; a second dialysate introduction line Lib; a first substitution line L2a; a second substitution line L2b; a pre-substitution line L2c; and a post-substitution line L2d; a first drain-liquid drain line Lia; a second drain-liquid drain line L3b; a blood pump P1; a dialysate introduction pump P2; a first substitution pump P3; a drain-liquid drain pump P4; a dialysate transfer pump P5; a substitution-fluid transfer pump P6; a drain-liquid transfer pump P7; a second substitution pump P8; an attaching unit D to which a substitution-fluid temporary chamber K1, a dialysate temporary chamber K2, and a drain-liquid temporary chamber K3 are attachable (the attaching unit D corresponds to a second supporting unit that supports the dialysate temporary chamber K2 and the substitution-fluid temporary chamber K1); a weighing device 4; a control unit 5; a first heating device H1; and a second heating device H2. Reference signs Pa and Pb given in the drawings each denote a pressure sensor. The blood pump P1, the dialysate introduction pump P2, the first substitution pump P3, the drain-liquid drain pump P4, the dialysate transfer pump P5, the substitution-fluid transfer pump P6, the drain-liquid transfer pump P7, and the second substitution pump P8 according to the present embodiment are each a peristaltic pump that delivers liquid by squeezing a flexible tube forming a flow route.

The arterial blood circuit 1a and the venous blood circuit 1b are provided at distal ends thereof with respective connectors, through which an arterial puncture needle and a venous puncture needle (not illustrated) are connectable thereto. When the blood pump P1 is activated while a patient is punctured with the arterial puncture needle connected to the distal end of the arterial blood circuit 1a and the venous puncture needle connected to the distal end of the venous blood circuit 1b, blood of the patient can be made to extracorporeally circulate through the blood circuit 1.

Specifically, when the blood pump P1 is activated while the patient is punctured with the arterial puncture needle and the venous puncture needle, the patient's blood flows through the arterial blood circuit 1a and reaches the dialyzer 2, where the blood is purified. Then, the blood flows through the venous blood circuit 1b and returns into the patient's body. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The venous blood circuit 1b is provided with an air-trap chamber 3 at a halfway position thereof. The blood that extracorporeally circulates through the blood circuit 1 undergoes bubble removal in the air-trap chamber 3 and then returns into the patient. As an alternative to the embodiment in which a blood vessel of the patient is punctured with the arterial puncture needle and the venous puncture needle, the following may be taken: an embodiment in which a double-lumen catheter is inserted into the subclavian vein or the femoral vein of the patient, an embodiment in which a double-lumen catheter is inserted into a blood vessel in an arm of the patient, or the like.

The dialyzer 2 has a blood introduction port 2a through which the blood is to be introduced thereinto, a blood delivery port 2b through which the blood is to be delivered therefrom, a dialysate introduction port 2c through which dialysate is to be introduced thereinto, a dialysate delivery port 2d through which the dialysate is to be delivered therefrom, blood flow routes (not illustrated) extending between the blood introduction port 2a and the blood delivery port 2b and through which the blood is to flow, dialysate flow routes (not illustrated) extending between the dialysate introduction port 2c and the dialysate delivery port 2d and through which the dialysate is to flow, and blood purification membranes (not illustrated) separating the blood flow routes from the dialysate flow routes and through which the blood flowing in the blood flow routes is to be purified.

More specifically, the dialyzer 2 has the blood introduction port 2a, the blood delivery port 2b, the dialysate introduction port 2c, and the dialysate delivery port 2d all projecting from a housing thereof. The arterial blood circuit 1a is connected to the blood introduction port 2a. The venous blood circuit 1b is connected to the blood delivery port 2b. The second dialysate introduction line L1b is connected to the dialysate introduction port 2c. The first drain-liquid drain line Lia is connected to the dialysate delivery port 2d. For efficient dialysis treatment, the blood introduction port 2a as the inlet for the blood and the dialysate introduction port 2c as the inlet for the dialysate are positioned on the opposite sides in the vertical direction, so that the dialysate flows in a direction opposite to the direction in which the blood flows through the blood flow routes.

The dialyzer 2 houses a plurality of hollow fiber membranes formed of hollow fibers, serving as blood purification membranes for purifying the blood. Specifically, spaces inside the respective blood purification membranes formed of the hollow fibers serve as the blood flow routes, and spaces between the housing and the hollow fibers serve as the dialysate flow routes. The blood purification membranes as the hollow fiber membranes each have a number of microscopic holes (pores) extending therethrough from the outer surface to the inner surface. Impurities and the like contained in the blood flowing in the blood flow routes are allowed to permeate (to be filtered) through the hollow fiber membranes into the dialysate flowing in the dialysate flow routes.

The first dialysate introduction line L1a is made of a flexible tube allowing the dialysate stored in a dialysate bag B1 (a dialysate storage) to flow into the dialysate temporary chamber K2. The first dialysate introduction line L1a has one end connected to the bottom of the dialysate bag B1 (the dialysate storage), and the other end connected to the bottom of the dialysate temporary chamber K2. The dialysate bag B1 stores a predetermined amount of dialysate to be supplied to the dialyzer 2. As illustrated in FIGS. 2 and 3, the dialysate bag B1 is supported at a predetermined height position by a supporting unit Q attached to an apparatus body. The dialysate temporary chamber K2 stores the dialysate received from the dialysate bag B1 (the dialysate storage) and is a case with a smaller capacity than the dialysate bag B1.

The first dialysate introduction line Da is provided with the dialysate transfer pump P5, which is a peristaltic pump that delivers liquid by squeezing a flexible tube forming a flow route for the dialysate. When the dialysate transfer pump P5 is activated, a rotor rotates and rollers squeeze the flexible tube in the lengthwise direction. Thus, the dialysate stored in the dialysate bag B1 can be delivered to and stored in the dialysate temporary chamber K2.

The second dialysate introduction line L1b is made of a flexible tube allowing the dialysate stored in the dialysate temporary chamber K2 to flow into the dialyzer 2. The second dialysate introduction line L1b has one end connected to the bottom of the dialysate temporary chamber K2, and the other end connected to the dialysate introduction port 2c of the dialyzer 2. The second dialysate introduction line L1b is provided with the dialysate introduction pump P2, which is a peristaltic pump that delivers liquid by squeezing a flexible tube forming a flow route for the dialysate. When the dialysate introduction pump P2 is activated, a rotor rotates and rollers squeeze the flexible tube in the lengthwise direction. Thus, the dialysate stored in the dialysate temporary chamber K2 can be delivered to and introduced into the dialyzer 2.

The second dialysate introduction line L1b according to the present embodiment is further provided with the heating device H1 for heating the dialysate. The heating device H1 is a heater capable of heating the dialysate to be introduced from the dialysate temporary chamber K2 into the dialyzer 2. A heating bag 6 is attachable to the heating device H1. The heating bag 6 has a flow route obtained by, for example, fusing two flexible sheets to each other. The flow route has connecting portions at one end and the other end thereof, respectively, where the flow route is connectable to the second dialysate introduction line Db.

The first substitution line L2a is made of a flexible tube allowing substitution fluid stored in a substitution-fluid bag B2 (a substitution-fluid storage) to flow into the substitution-fluid temporary chamber K1. The first substitution line L2a has one end connected to the bottom of the substitution-fluid bag B2 (the substitution-fluid storage), and the other end connected to the bottom of the substitution-fluid temporary chamber K1. The substitution-fluid bag B2 stores a predetermined amount of substitution fluid to be supplied to the blood circuit 1. As illustrated in FIGS. 2 and 3, the substitution-fluid bag B2 is supported at a predetermined height position by the supporting unit Q attached to the apparatus body. The substitution-fluid temporary chamber K1 stores the substitution fluid received from the substitution-fluid bag B2 (the substitution-fluid storage) and is a case with a smaller capacity than the substitution-fluid bag B2.

The first substitution line L2a is provided with the substitution-fluid transfer pump P6, which is a peristaltic pump that delivers liquid by squeezing a flexible tube forming a flow route for the substitution fluid. When the substitution-fluid transfer pump P6 is activated, a rotor rotates and rollers squeeze the flexible tube in the lengthwise direction. Thus, the substitution fluid stored in the substitution-fluid bag B2 can be delivered to and stored in the substitution-fluid temporary chamber K1.

The second substitution line L2b is made of a flexible tube that allows the substitution fluid stored in the substitution-fluid temporary chamber K1 to flow into the blood circuit 1 through the pre-substitution line L2c or the post-substitution line L2d. The second substitution line L2b has one end connected to the bottom of the substitution-fluid temporary chamber K1, and the other end connected to the pre-substitution line L2c and to the post-substitution line L2d. The second substitution line L2b is provided with the first substitution pump P3, which is a peristaltic pump that delivers liquid by squeezing a flexible tube forming a flow route for the substitution fluid. When the first substitution pump P3 is activated, a rotor rotates and rollers squeeze the flexible tube in the lengthwise direction. Thus, the substitution fluid stored in the substitution-fluid temporary chamber K1 can be delivered for substitution to the arterial blood circuit 1a through the pre-substitution line L2c or to the venous blood circuit 1b through the post-substitution line L2d.

The second substitution line L2b according to the present embodiment is further provided with the heating device H2 for heating the substitution fluid. The heating device H2 is a heater capable of heating the substitution fluid to be introduced from the substitution-fluid temporary chamber K1 into the blood circuit 1. A heating bag 6 illustrated in FIG. 1 is attachable to the heating device H2. The heating bag 6 has a flow route obtained by, for example, fusing two flexible sheets to each other. The flow route has connecting portions at one end and the other end thereof, respectively, where the flow route is connectable to the second substitution line L2b.

The second substitution line L2b is further provided with an air-trap chamber 7 at a position between the heating device H2 and the arterial blood circuit 1a or the venous blood circuit 1b. The air-trap chamber 7 is capable of trapping bubbles in the substitution fluid. The bubbles in the substitution fluid heated by the heating device H2 are trapped in the air-trap chamber 7 and are therefore prevented from flowing into the blood circuit 1. The air-trap chamber 7 is provided at the top thereof with a connection line L4 to which the pressure sensor Pb is attached. Therefore, the hydraulic pressure of the substitution fluid flowing in the second substitution line L2b is detectable through an air layer in the air-trap chamber 7. The connection line L4 is provided with an air filter F4.

The pre-substitution line L2c is a flow route through which the substitution fluid is introduced into the arterial blood circuit 1a for pre-substitution. The pre-substitution line L2c has one end connected to the second substitution line L2b, and the other end connected to a position of the arterial blood circuit 1a that is between the blood pump P1 and the dialyzer 2. When the first substitution pump P3 is activated and the substitution fluid is delivered from the substitution-fluid temporary chamber K1 through the second substitution line L2b, the substitution fluid flows through the pre-substitution line L2c into the arterial blood circuit 1a.

The post-substitution line L2d is a flow route through which the substitution fluid is introduced into the venous blood circuit 1b for post-substitution. The post-substitution line L2d has one end connected to the second substitution line L2b, and the other end connected to the air-trap chamber 3 provided to the venous blood circuit 1b. When the first substitution pump P3 is activated and the substitution fluid is delivered from the substitution-fluid temporary chamber K1 through the second substitution line L2b, the substitution fluid flows through the post-substitution line L2d into the venous blood circuit 1b.

The pre-substitution line L2c according to the present embodiment is provided with the second substitution pump P8, which is a peristaltic pump that delivers liquid by squeezing a flexible tube forming a flow route for the substitution fluid. The post-substitution line L2d is provided with a check valve V1 that allows the substitution fluid to flow toward the blood circuit 1 but prevents the substitution fluid from flowing toward the other side. The substitution pumps according to the present embodiment include the first substitution pump P3 provided to the substitution line (the second substitution line L2b) and the second substitution pump P8 provided to at least one of the pre-substitution line L2c and the post-substitution line L2d (in the present embodiment, the pre-substitution line L2c).

Hence, when the second substitution pump P8 is activated at substantially the same flow rate as that of the first substitution pump P3, the substitution fluid in the substitution-fluid temporary chamber K1 can be introduced into the arterial blood circuit 1a for pre-substitution. On the other hand, when the first substitution pump P3 is activated with the second substitution pump P8 stopped, the substitution fluid in the substitution-fluid temporary chamber K1 can be introduced into the venous blood circuit 1b for post-substitution. Furthermore, when the second substitution pump P8 is activated at a flow rate lower than that of the first substitution pump P3, the substitution fluid can be introduced into both the arterial blood circuit 1a and the venous blood circuit 1b for pre- and post-substitution. The control unit 5 is capable of changing the ratio between the amount of pre-substitution and the amount of post-substitution by controlling the first substitution pump P3 and the second substitution pump P8 in such a manner as to change the flow-rate ratio between the first substitution pump P3 and the second substitution pump P8.

The post-substitution line L2d is provided with the check valve V1. Therefore, even if a negative pressure is generated in the flow route between the first substitution pump P3 and the second substitution pump P8, the blood in the blood circuit 1 can be prevented from being taken into the post-substitution line L2d. Note that a negative pressure is generated in the flow route between the first substitution pump P3 and the second substitution pump P8 when the flow rate of the second substitution pump P8 is higher than the flow rate of the first substitution pump P3. Other possible embodiments are as follows: an embodiment in which the pre-substitution line L2c is provided with the check valve V1 while the post-substitution line L2d is provided with the second substitution pump P8, and an embodiment in which the pre-substitution line L2c and the post-substitution line L2d are each provided with the second substitution pump P8.

The blood purification apparatus further includes the pressure sensor Pb that detects the hydraulic pressure in a portion of the flow route for the substitution fluid, the portion being enclosed by the first substitution pump P3, the second substitution pump P8, and the check valve V1 in the second substitution line L2b (the substitution line), the pre-substitution line L2c, and the post-substitution line L2d. The control unit 5 corrects the driving speed of the first substitution pump P3 or the second substitution pump P8 in accordance with the hydraulic pressure detected by the pressure sensor Pb.

The first drain-liquid drain line L3a is made of a flexible tube that allows the drain liquid drained from the dialyzer 2 to flow into the drain-liquid temporary chamber K3. The first drain-liquid drain line L3a has one end connected to the dialysate delivery port 2d of the dialyzer 2, and the other end connected to the bottom of the drain-liquid temporary chamber K3. The drain-liquid temporary chamber K3 stores the drain liquid drained from the dialyzer 2 and is a case with a substantially equal capacity to those of the dialysate temporary chamber K2 and the substitution-fluid temporary chamber K1.

The first drain-liquid drain line L3a is provided with the drain-liquid drain pump P4, which is a peristaltic pump that delivers liquid by squeezing a flexible tube forming a flow route for the drain liquid. When the drain-liquid drain pump P4 is activated, a rotor rotates and rollers squeeze the flexible tube in the lengthwise direction. Thus, the drain liquid in the dialyzer 2 can be delivered to and stored in the drain-liquid temporary chamber K3.

The second drain-liquid drain line L3b is made of a flexible tube that allows the drain liquid stored in the drain-liquid temporary chamber K3 to be drained to the outside of the apparatus. The second drain-liquid drain line L3b has one end connected to the bottom of the drain-liquid temporary chamber K3, and the other end reaching a device, such as a processing device or a drain pan, provided on the outside of the apparatus. A combination of the first substitution line L2a and the second substitution line L2b corresponds to the substitution line according to the present invention.

The second drain-liquid drain line L3b is provided with the drain-liquid transfer pump P7, which is a peristaltic pump that delivers liquid by squeezing a flexible tube forming a flow route for the drain liquid. The drain-liquid transfer pump P7 (a draining unit) is a pump that drains the drain liquid stored in the drain-liquid temporary chamber K3 to the outside of the apparatus at an arbitrary timing. When the drain-liquid transfer pump P7 is activated, a rotor rotates and rollers squeeze the flexible tube in the lengthwise direction. Thus, the drain liquid in the drain-liquid temporary chamber K3 can be drained to the outside of the apparatus.

Figure 4:
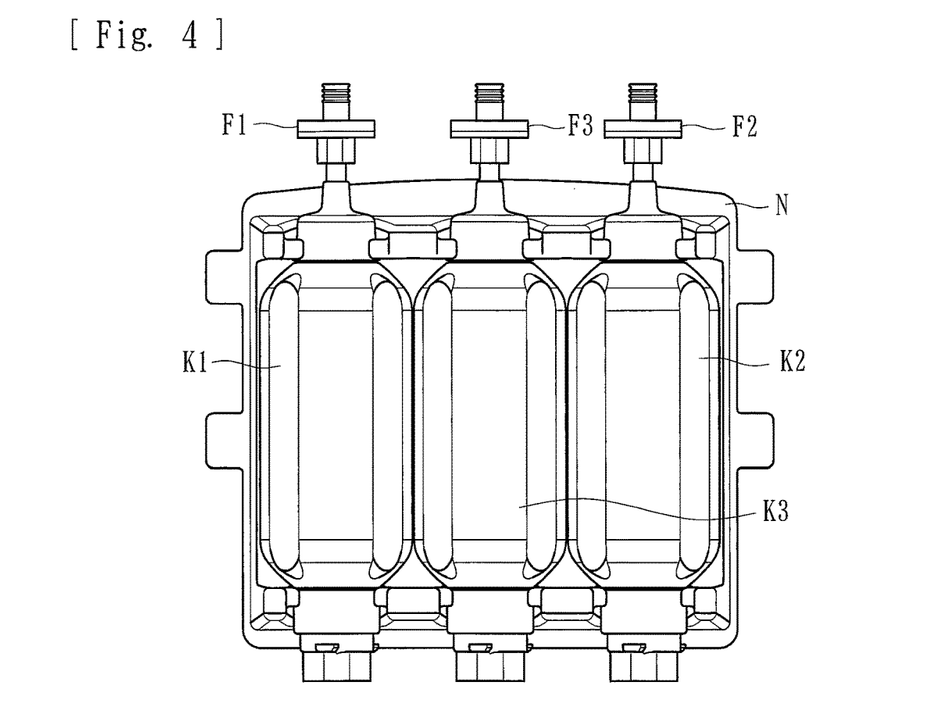
FIG. 4 is a front view of the temporary chambers included in the blood purification apparatus.
Figure 5:
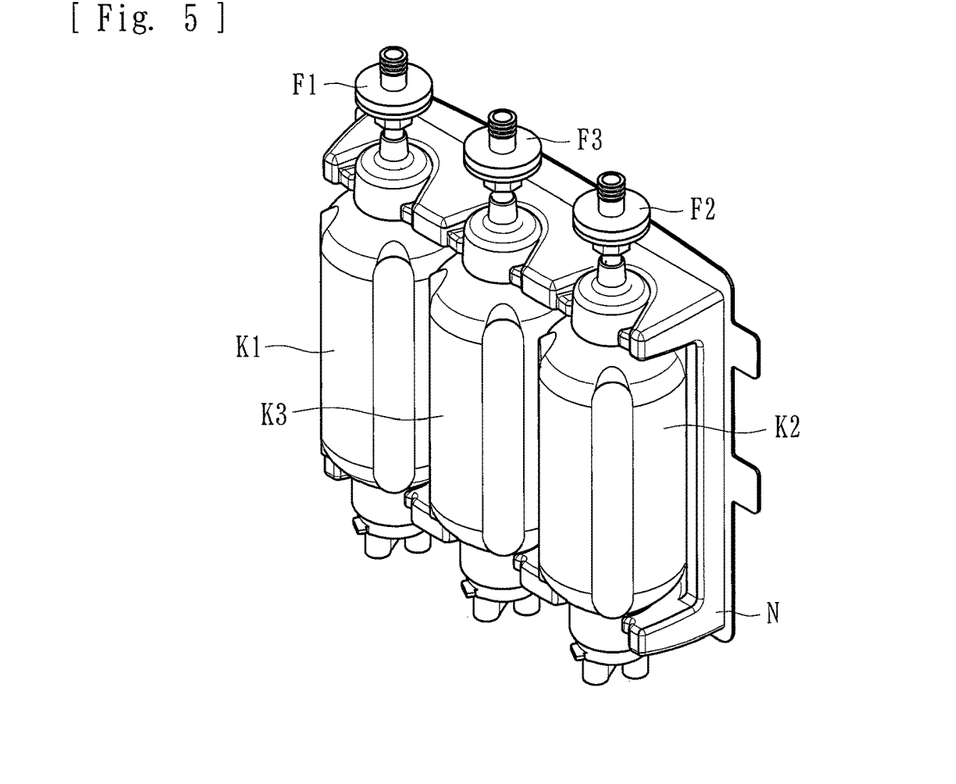
FIG. 5 is a perspective view of the temporary chambers.

As illustrated in FIGS. 4 and 5, the dialysate temporary chamber K2, the substitution-fluid temporary chamber K1, and the drain-liquid temporary chamber K3 are held by a holding unit N and are thus attached to the attaching unit D, which is to be described below. The top of each of the dialysate temporary chamber K2, the substitution-fluid temporary chamber K1, and the drain-liquid temporary chamber K3 is open to the atmosphere through a corresponding one of air filters F1 to F3. Therefore, if some liquid stored in the temporary chamber is discharged therefrom, some air is introduced into the temporary chamber. If some liquid flows into the temporary chamber, some air in the temporary chamber is discharged therefrom.

As illustrated in FIGS. 2 and 3, the blood purification apparatus according to the present embodiment includes the supporting unit Q that supports the dialysate bag B1 and the substitution-fluid bag B2 at a predetermined height position; a monitor M that is capable of displaying information regarding the treatment and the like; an enclosure G that encloses the dialysate introduction pump P2, the first substitution pump P3, the drain-liquid drain pump P4, the dialysate transfer pump P5, the substitution-fluid transfer pump P6, the drain-liquid transfer pump P7, and the second substitution pump P8; and the attaching unit D.

Figure 7:
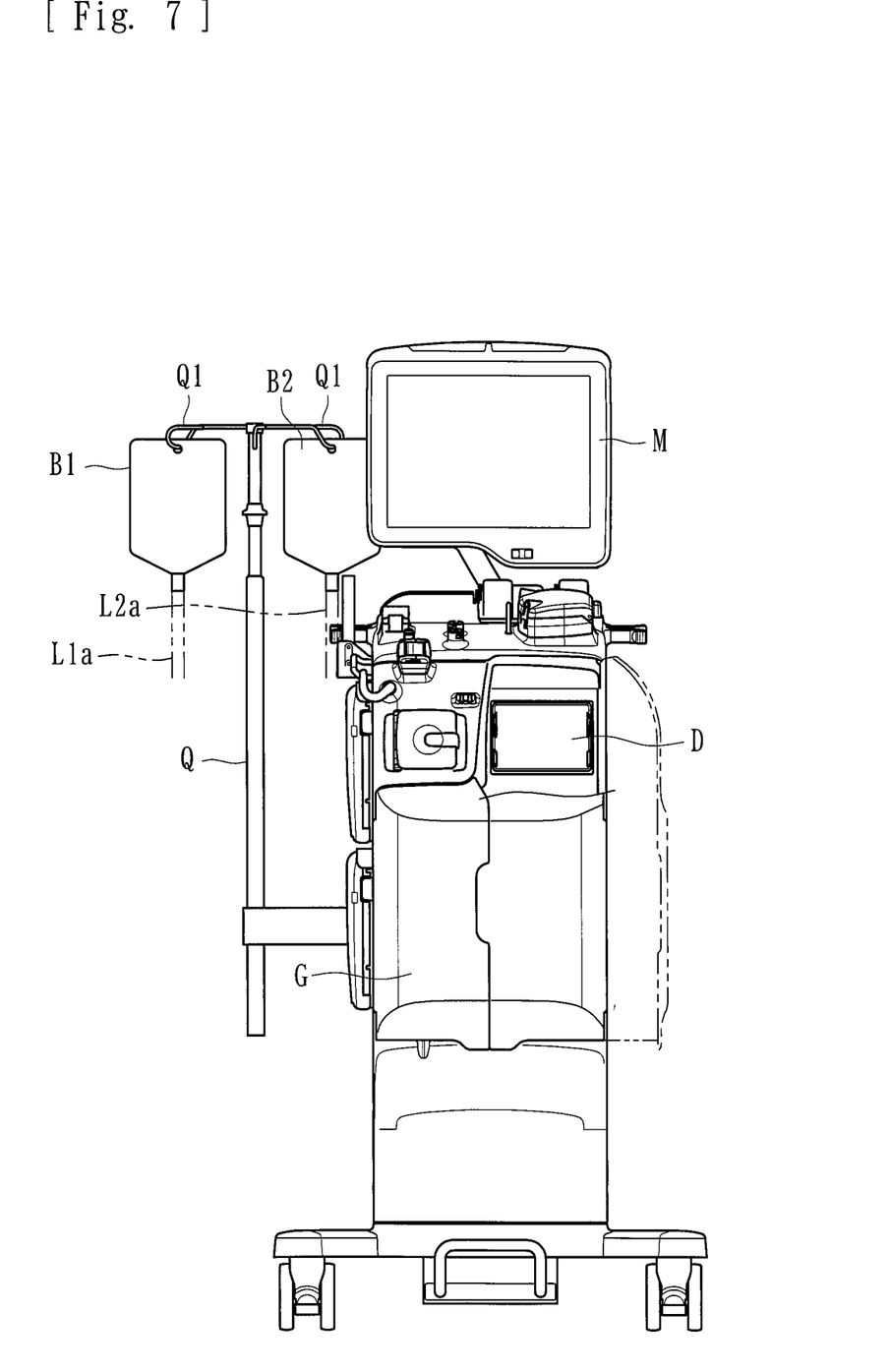
FIG. 7 is a front view of the blood purification apparatus, with the height position of a supporting unit thereof changed (to a low supporting position).

The supporting unit Q (a first supporting unit) is a pole-like member attached to the apparatus body and includes hanging portions Q1 capable of supporting the dialysate bag B1 and the substitution-fluid bag B2 at the predetermined height position, and a locking portion R operable in changing the height position. Specifically, the supporting unit Q according to the present embodiment is extendable and contractible in the lengthwise direction, so that the height position where the dialysate bag B1 and the substitution-fluid bag B2 are supported can be adjusted arbitrarily. Note that FIGS. 2 and 3 each illustrate a state where the dialysate bag B1 and the substitution-fluid bag B2 are supported at a high position with the supporting unit Q extended, while FIG. 7 illustrates a state where the dialysate bag B1 and the substitution-fluid bag B2 are supported at a low position with the supporting unit Q contracted.

The locking portion R of the supporting unit Q is capable of locking and unlocking an upper part and a lower part of the supporting unit Q to and from each other. The height position of the hanging portions Q1 is adjustable in an unlocked state by sliding the upper part relative to the lower part. After the height position of the hanging portions Q1 is adjusted, the locking portion R is operated to lock the upper part of the supporting unit Q to the lower part, so that the dialysate bag B1 and the substitution-fluid bag B2 can be hung on the hanging portions Q1.

Figure 6:
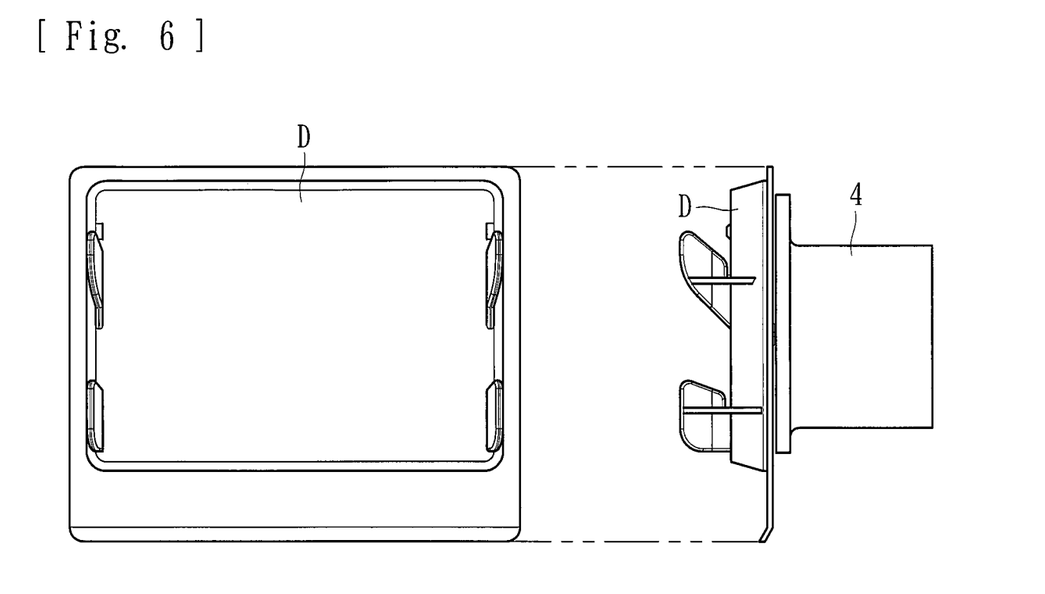
FIG. 6 includes a front view and a side view of an attaching unit included in the blood purification apparatus and to which the temporary chambers are attached.

As illustrated in FIG. 3, the holding unit N holding the temporary chambers (the dialysate temporary chamber K2, the substitution-fluid temporary chamber K1, and the drain-liquid temporary chamber K3) is attachable to the attaching unit D (the second supporting unit). As illustrated in FIG. 6, the weight of the dialysate temporary chamber K2, the substitution-fluid temporary chamber K1, and the drain-liquid temporary chamber K3 is to be measured by a weighing device 4 (a weight sensor) attached to the back of the attaching unit D. Thus, the weight balance between the dialysate, the substitution fluid, and the drain liquid stored in the dialysate temporary chamber K2, the substitution-fluid temporary chamber K1, and the drain-liquid temporary chamber K3 is detectable in real time for monitoring.

The attaching unit D is further provided with a liquid-level sensor S1 that detects the reaching of the liquid surface in the dialysate temporary chamber K2 to a specified level (i.e., a situation where the amount of dialysate stored therein has reached a specified value), and a liquid-level sensor S2 that detects the reaching of the liquid surface in the substitution-fluid temporary chamber K1 to a specified level (i.e., a situation where the amount of substitution fluid stored therein has reached a specified value). Thus, a situation where the dialysate temporary chamber K2 or the substitution-fluid temporary chamber K1 has become full (a situation where the amount of dialysate or substitution fluid has reached a specified value or greater) is detectable.

The control unit 5 controls various actuators such as the dialysate introduction pump P2, the first substitution pump P3, the drain-liquid drain pump P4, the dialysate transfer pump P5, the substitution-fluid transfer pump P6, the drain-liquid transfer pump P7, and the second substitution pump P8 in accordance with the value measured by the weighing device 4. The control unit 5 is a microcomputer or the like provided on the apparatus body. The control unit 5 according to the present embodiment executes an initialization step in which the amount of dialysate in the dialysate temporary chamber K2 and the amount of substitution fluid in the substitution-fluid temporary chamber K1 are increased to respective specified values or greater (a full state), and the amount of drain liquid in the drain-liquid temporary chamber K3 is reduced to a specified value or smaller (an initialized state) by draining the drain liquid with the drain-liquid transfer pump P7 (the draining unit); and a measurement step in which the dialysate in the dialysate temporary chamber K2, the substitution fluid in the substitution-fluid temporary chamber K1, and the drain liquid in the drain-liquid temporary chamber K3 are weighed with the weighing device 4. Note that the initialized state of the drain-liquid temporary chamber K3 is desirably, but is not limited to, a state established immediately before the drain-liquid temporary chamber K3 becomes completely empty and may be specified by any value.

Specifically, in the measurement step, the dialysate introduction pump P2 is activated to introduce the dialysate stored in the dialysate temporary chamber K2 into the dialyzer 2, the first substitution pump P3 (and the second substitution pump P8, according to need) is activated to introduce the substitution fluid stored in the substitution-fluid temporary chamber K1 into the blood circuit 1, and the drain-liquid drain pump P4 is activated to store the drain liquid drained from the dialyzer 2 in the drain-liquid temporary chamber K3. In this step, the dialysate transfer pump P5, the substitution-fluid transfer pump P6, and the drain-liquid transfer pump P7 are stopped.

In the measurement step, the weight balance between the dialysate, the substitution fluid, and the drain liquid stored in the dialysate temporary chamber K2, the substitution-fluid temporary chamber K1, and the drain-liquid temporary chamber K3 is detectable in real time by the weighing device 4 for monitoring. Therefore, the weight balance between the dialysate, the substitution fluid, and the drain liquid can be set to a desired level by controlling the operation of the dialysate introduction pump P2, the first substitution pump P3 (and the second substitution pump P8), and the drain-liquid drain pump P4 in accordance with the value measured by the weighing device 4. Thus, normal treatment can be achieved.

In the above measurement step, when it is detected that the total amount of flow generated by the dialysate introduction pump P2, the first substitution pump P3 (and the second substitution pump P8, according to need), and the drain-liquid drain pump P4 has reached a predetermined value and the dialysate temporary chamber K2 and the substitution-fluid temporary chamber K1 have been initialized (the amounts of liquids therein are reduced to the specified values or smaller) while the drain-liquid temporary chamber K3 has become full (the amount of liquid therein is increased to the specified value or greater), the operation is shifted to the initialization step.

In the initialization step, while the dialysate introduction pump P2, the first substitution pump P3 (and the second substitution pump P8, according to need), and the drain-liquid drain pump P4 are kept active, the dialysate transfer pump P5, the substitution-fluid transfer pump P6, and the drain-liquid transfer pump P7 are activated. Thus, the active dialysate transfer pump P5 causes the dialysate in the dialysate bag B1 to flow into and be stored in the dialysate temporary chamber K2, the active substitution-fluid transfer pump P6 causes the substitution fluid in the substitution-fluid bag B2 to flow into and be stored in the substitution-fluid temporary chamber K1, and the active drain-liquid transfer pump P7 causes the drain liquid in the drain-liquid temporary chamber K3 to be drained to the outside of the apparatus.

Furthermore, the liquid-level sensors S1 and S2 are provided for detecting the liquid surfaces in the dialysate temporary chamber K2 and the substitution-fluid temporary chamber K1, respectively. Therefore, the reaching of the amounts of dialysate and substitution fluid stored in the dialysate temporary chamber K2 and the substitution-fluid temporary chamber K1 to the respective specified levels is detectable. In such a case, since no liquid-level sensor that detects the liquid surface in the drain-liquid temporary chamber K3 is provided, a situation where the drain-liquid temporary chamber K3 has been initialized (the reaching of the amount of liquid to a specified value or smaller) cannot be detected directly.

Hence, according to the present embodiment, the reaching of the amounts of dialysate and substitution fluid to the specified values is detected in the initialization step by using the liquid-level sensors S1 and S2. Then, after the reaching of the amounts of dialysate and substitution fluid to the specified values (the full state) is detected, if the total weight (the value measured by the weighing device 4) of the dialysate, the substitution fluid, and the drain liquid in the dialysate temporary chamber K2, the substitution-fluid temporary chamber K1, and the drain-liquid temporary chamber K3 that is measured by the weighing device 4 is reduced to the specified value or smaller (the initialized state), the draining of the drain liquid by the drain-liquid transfer pump P7 (the draining unit) is ended to shift the operation to the measurement step.

Hence, even if no liquid-level sensor that detects the liquid surface in the drain-liquid temporary chamber K3 is provided, the draining of the drain liquid can be ended when the drain-liquid temporary chamber K3 is initialized (when the amount of liquid is reduced to the specified value or smaller). Such a configuration can prevent the occurrence of insufficient draining of the drain liquid, or mixing of air due to lowering of the drain-liquid surface to the first drain-liquid drain line Lia or the second drain-liquid drain line L3b with continued operation of the drain-liquid transfer pump P7 even after the initialization.

In addition to the above condition, in the initialization step, if the total amount of flow (the total number of revolutions of the rotor) generated by the drain-liquid transfer pump P7 (the draining unit) has reached the total amount of flow (the total number of revolutions of the rotor) generated by the drain-liquid transfer pump P7 in the previous measurement step, the control unit 5 may shift the operation to the measurement step. In such a configuration, the drain liquid in the drain-liquid temporary chamber K3 can be drained more accurately.

The control unit 5 according to the present embodiment may alternatively be a unit that controls the flow rate of the dialysate transfer pump P5 in accordance with the flow rate of the dialysate introduction pump P2, or a unit that sets the flow rate of the dialysate introduction pump to a value greater than 6000 mL/h. Furthermore, the height-position difference between the bottom of the dialysate bag B1 and the top of the dialysate temporary chamber K2 and the height-position difference between the bottom of the substitution-fluid bag B2 and the top of the substitution-fluid temporary chamber K1 may each be smaller than 40 cm, or the height position at the bottoms of the dialysate bag B1 and the substitution-fluid bag B2 may be lower than 160 cm. Furthermore, the reaching of the amount of liquid in the dialysate temporary chamber K2 or the substitution-fluid temporary chamber K1 to the specified value (the reaching to the full state) may be identified by the total amount of flow generated by the dialysate transfer pump P5 or the substitution-fluid transfer pump P6.

According to the present embodiment, the blood purification apparatus includes the dialysate transfer pump P5 provided to the first dialysate introduction line L1a and that transfers the dialysate in the dialysate bag B1 to the dialysate temporary chamber K2, the substitution-fluid transfer pump P6 provided to the first substitution line L2a and that transfers the substitution fluid in the substitution-fluid bag B2 to the substitution-fluid temporary chamber K1, and the control unit 5 that controls the dialysate transfer pump P5 and the substitution-fluid transfer pump P6. Therefore, the transfer from the dialysate bag B1 and the substitution-fluid bag B2 to the dialysate temporary chamber K2 and the substitution-fluid temporary chamber K1, respectively, can be achieved in a good manner, and the degree of freedom in the layout of the dialysate bag B1 and the substitution-fluid bag B2 can be increased.

The blood purification apparatus further includes the drain-liquid temporary chamber K3 that stores the drain liquid received from the dialyzer 2, the drain-liquid drain line (the second drain-liquid drain line L3b) through which the drain liquid in the drain-liquid temporary chamber K3 is drained to the outside of the apparatus, and the drain-liquid transfer pump P7 provided to the drain-liquid drain line (the second drain-liquid drain line L3b) and that transfers the drain liquid in the drain-liquid temporary chamber K3 to the outside of the apparatus. The control unit 5 controls the drain-liquid transfer pump P7 in addition to the dialysate transfer pump P5 and the substitution-fluid transfer pump P6. Therefore, no limit is imposed on the height position of the drain-liquid temporary chamber K3, and the degree of freedom in the layout of the drain-liquid temporary chamber K3 in addition to the degree of freedom in the layout of the dialysate bag B1 and the substitution-fluid bag B2 can be increased.

The dialysate transfer pump P5, the substitution-fluid transfer pump P6, and the drain-liquid transfer pump P7 are each a peristaltic pump that delivers liquid by squeezing the flexible tube forming the flow route for a corresponding one of the dialysate, the substitution fluid, and the drain liquid. Therefore, the flow route for each of the dialysate, the substitution fluid, and the drain liquid can be closed by stopping the peristaltic pump, with no need to provide any separate clamp unit or the like.

If the blood purification apparatus further includes the second dialysate introduction line L1b through which the dialysate in the dialysate temporary chamber K2 flows into the dialyzer 2; and the dialysate introduction pump P2 provided to the second dialysate introduction line L1b and that delivers the dialysate in the dialysate temporary chamber K2 to the dialyzer 2, and if the control unit 5 controls the flow rate of the dialysate transfer pump P5 in accordance with the flow rate of the dialysate introduction pump P2, the flow rate of the dialysate to be transferred to the dialysate temporary chamber K2 can be made greater than the flow rate of the dialysate to be introduced from the dialysate temporary chamber K2 into the dialyzer 2. Consequently, the occurrence of shortage of the dialysate in the dialysate temporary chamber K2 can be avoided assuredly.

If the flow rate of the dialysate introduction pump P2 is set to a value greater than 6000 mUh, the dialysis efficiency in the blood purification treatment can be increased. Furthermore, if the height-position difference between the bottom of the dialysate bag B1 supported by the supporting unit Q (the first supporting unit) and the top of the dialysate temporary chamber K2 supported by the attaching unit D (the second supporting unit) and the height-position difference between the bottom of the substitution-fluid bag B2 supported by the supporting unit Q (the first supporting unit) and the top of the substitution-fluid temporary chamber K1 supported by the attaching unit D (the second supporting unit) are each set to a value smaller than 40 cm, the ease of work in replacing the dialysate bag B1 and the substitution-fluid bag B2 with new ones can be increased. If the height position at the bottoms of the dialysate bag B1 and the substitution-fluid bag B2 supported by the supporting unit Q (the first supporting unit) is set to a value lower than 160 cm, the ease of work in replacing the dialysate bag B1 and the substitution-fluid bag B2 with new ones can be increased further.

The supporting unit Q (the first supporting unit) is configured such that the height position where at least one of the dialysate bag B1 and the substitution-fluid bag B2 is supported is adjustable. Therefore, it is easy to support the dialysate bag B1 and the substitution-fluid bag B2 at respective positions corresponding to the layout of the dialysate bag B1 and the substitution-fluid bag B2.

If the reaching of the amount of liquid in the dialysate temporary chamber K2 or the substitution-fluid temporary chamber K1 to the specified value is identified by the total amount of flow generated by the dialysate transfer pump P5 or the substitution-fluid transfer pump P6, the situation where the dialysate temporary chamber K2 or the substitution-fluid temporary chamber K1 has become full can be detected without providing the liquid-level sensors S1 and S2. In particular, according to the present embodiment, after the reaching of the amounts of dialysate and substitution fluid to the specified values is detected in the initialization step, if the total weight of the dialysate, the substitution fluid, and the drain liquid in the dialysate temporary chamber K2, the substitution-fluid temporary chamber K1, and the drain-liquid temporary chamber K3 that is measured by the weighing device 4 is reduced to a value smaller than the specified value, the draining of the drain liquid by the drain-liquid transfer pump P7 (the draining unit) is ended to shift the operation to the measurement step. Therefore, in the initialization step, the situation where the drain-liquid temporary chamber K3 has been initialized can be grasped correctly, without the detection of the liquid surface in the drain-liquid temporary chamber K3.

The blood purification apparatus further includes the liquid-level sensor S2 (a detecting unit) that detects the reaching of the amount of liquid in the dialysate temporary chamber K2 to the specified value. Furthermore, the control unit 5 stops the dialysate transfer pump P5 when the reaching of the amount of liquid in the dialysate temporary chamber K2 to the specified value is detected by the liquid-level sensor S2. Therefore, the supply of the dialysate from the dialysate bag B1 can be achieved in a good manner. The blood purification apparatus further includes the liquid-level sensor S1 (a detecting unit) that detects the reaching of the amount of liquid in the substitution-fluid temporary chamber K1 to the specified value. Furthermore, the control unit 5 stops the substitution-fluid transfer pump P6 when the reaching of the amount of liquid in the substitution temporary chamber K1 to the specified value is detected by the liquid-level sensor S1. Therefore, the supply of the substitution fluid from the substitution-fluid bag B2 can be achieved in a good manner.

The blood purification apparatus includes the liquid-level sensors S1 and S2 that detect the reaching of the dialysate and the substitution fluid in the dialysate temporary chamber K2 and the substitution-fluid temporary chamber K1 to the respective specified values. Furthermore, in the initialization step, after the reaching of the amounts of dialysate and substitution fluid to the specified values is detected by the liquid-level sensors S1 and S2, if the total weight of the dialysate, the substitution fluid, and the drain liquid in the dialysate temporary chamber K2, the substitution-fluid temporary chamber K1, and the drain-liquid temporary chamber K3 that is measured by the weighing device 4 is reduced to a value smaller than the specified value, the control unit 5 shifts the operation to the measurement step. Therefore, in the initialization step, the situation where the dialysate temporary chamber K2 and the substitution-fluid temporary chamber K1 have become full can be grasped correctly, and the situation where the drain-liquid temporary chamber K3 has been initialized can be grasped correctly.

The draining unit that drains the drain liquid from the drain-liquid temporary chamber K3 is provided as the drain-liquid transfer pump P7 that drains the drain liquid stored in the drain-liquid temporary chamber K3 to the outside of the apparatus at an arbitrary timing. Therefore, the draining of the drain liquid from the drain-liquid temporary chamber K3 in the initialization step can be achieved smoothly. Furthermore, if the flow rate of the drain-liquid transfer pump P7 is controlled, the duration of draining the drain liquid can be adjusted arbitrarily.

Figure 9:
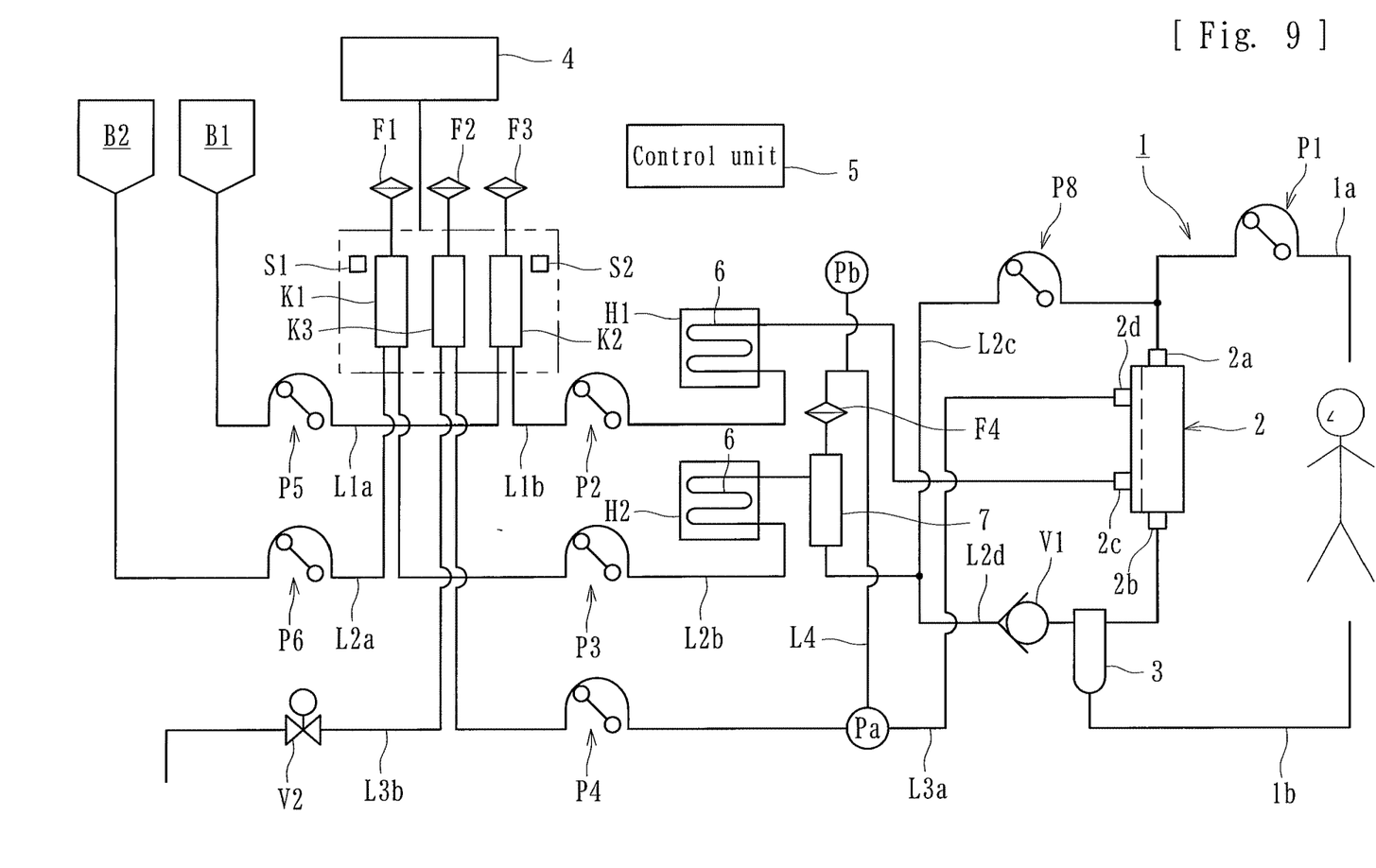
FIG. 9 is a schematic diagram of a blood purification apparatus according to yet another embodiment of the present invention (including an electromagnetic valve as a draining unit).

While some embodiments have been described above, the present invention is not limited thereto. For example, another embodiment illustrated in FIG. 9 may be employed in which the draining unit provided to the second drain-liquid drain line L3b and that drains the drain liquid stored in the drain-liquid temporary chamber K3 to the outside of the apparatus at an arbitrary timing is an electromagnetic valve V2 that is controlled to be opened or closed by the control unit 5. In such an embodiment, the initialization step is executed with the electromagnetic valve V2 being open so as to drain the drain liquid to the outside of the apparatus. Thus, the amount of drain liquid in the drain-liquid temporary chamber K3 can be reduced to the specified value or smaller (the initialized state). The electromagnetic valve V2 may be replaced with another clamp unit capable of opening and closing the flow route as the second drain-liquid drain line L3b.

The above embodiments each concern a case where a single weighing device 4 measures the total weight of the dialysate, the substitution fluid, and the drain liquid in the dialysate temporary chamber K2, the substitution-fluid temporary chamber K1, and the drain-liquid temporary chamber K3 and detects the weight balance therebetween for monitoring. Alternatively, plural weighing devices may be provided for measuring the respective weights of the dialysate, the substitution fluid, and the drain liquid in the dialysate temporary chamber K2, the substitution-fluid temporary chamber K1, and the drain-liquid temporary chamber K3.

Figure 8:
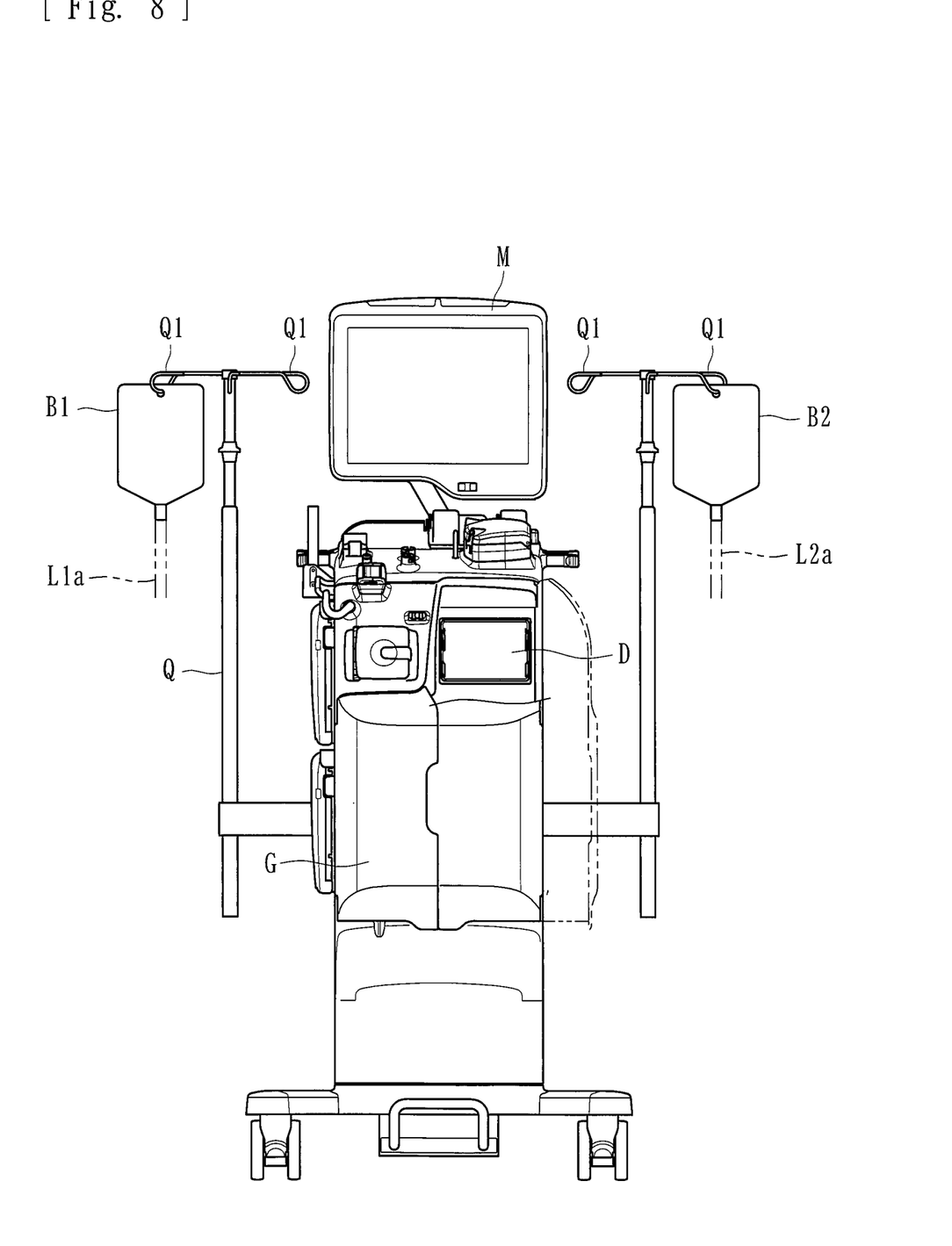
FIG. 8 is a schematic diagram of a blood purification apparatus according to another embodiment of the present invention (including supporting units that support a dialysate storage and a substitution-fluid storage, respectively).

As illustrated in FIG. 8, the blood purification apparatus may include a supporting unit Q1 that supports the dialysate bag B1, and a supporting unit Q2 that supports the substitution-fluid bag B2. In such a case, the height position of the dialysate bag B1 and the height position of the substitution-fluid bag B2 can be adjusted independently of each other. Consequently, the ease of layout of the dialysate bag B1 and the substitution-fluid bag B2 can be increased further. The dialysate bag B1 and the substitution-fluid bag B2, which are each a flexible case, may be replaced with a dialysate storage and a substitution-fluid storage each being a hard case, a liquid tank, or the like.

The blood purification apparatus may have other additional functions or the like, as long as the apparatus includes a dialysate transfer pump provided to a first dialysate introduction line and that transfers dialysate in a dialysate storage to a dialysate temporary chamber, a substitution-fluid transfer pump provided to a substitution line and that transfers substitution fluid in a substitution-fluid storage to a substitution-fluid temporary chamber, and a control unit that controls the dialysate transfer pump and the substitution-fluid transfer pump.

REFERENCE SIGN LIST 1 blood circuit
1a arterial blood circuit
1b venous blood circuit
2 dialyzer (blood purifier)
3 air-trap chamber
4 weighing device
5 control unit
6 heating bag
7 air-trap chamber
K1 substitution-fluid temporary chamber
K2 dialysate temporary chamber
K3 drain-liquid temporary chamber
B1 dialysate bag (dialysate storage)
B2 substitution-fluid bag (substitution-fluid storage)
L1a first dialysate introduction line
L1b second dialysate introduction line
L2a first substitution line
L2b second substitution line
L2c pre-substitution line
L2d post-substitution line
L1a first drain-liquid drain line
L3b second drain-liquid drain line
P1 blood pump
P2 dialysate introduction pump
P3 first substitution pump
P4 drain-liquid drain pump
P5 dialysate transfer pump
P6 substitution-fluid transfer pump
P7 drain-liquid transfer pump (draining unit)
P8 second substitution pump
H1 first heating device
H2 second heating device
S1, S2 liquid-level sensor
Pa, Pb pressure sensor
D attaching unit (second supporting unit)
Q supporting unit (first supporting unit)

What is claimed is:

1. A blood purification apparatus that includes:
a blood circuit including an arterial blood circuit and a venous blood circuit and that allows a patient's blood to extracorporeally circulate, with a blood purifier that is interposed between the arterial blood circuit and the venous blood circuit and purifies the patient's blood;
a dialysate temporary chamber that temporarily stores dialysate received from a dialysate storage supported by a supporting unit;
a substitution-fluid temporary chamber that temporarily stores substitution fluid received from a substitution-fluid storage supported by the supporting unit;
a first dialysate introduction line through which the dialysate in the dialysate storage flows into the dialysate temporary chamber; and
a substitution line through which the substitution fluid in the substitution-fluid storage flows into the substitution-fluid temporary chamber,
the blood purification apparatus comprising:
a dialysate transfer pump provided to the first dialysate introduction line and that transfers the dialysate in the dialysate storage to the dialysate temporary chamber;
a substitution-fluid transfer pump provided to the substitution line and that transfers the substitution fluid in the substitution-fluid storage to the substitution-fluid temporary chamber;
a control unit configured to control the dialysate transfer pump and the substitution-fluid transfer pump;

a drain-liquid temporary chamber that stores drain liquid received from the blood purifier;

a drain-liquid drain line through which the drain liquid in the drain-liquid temporary chamber is drained to an outside of the blood purification apparatus;

a drain-liquid transfer pump provided to the drain-liquid drain line and that transfers the drain liquid in the drain-liquid temporary chamber to the outside of the blood purification apparatus, a second dialysate introduction line through which the dialysate in the dialysate temporary chamber flows into the blood purifier; and a dialysate introduction pump provided to the second dialysate introduction line and that delivers the dialysate in the dialysate temporary chamber to the blood purifier, wherein the control unit configured to control the drain-liquid transfer pump in addition to the dialysate transfer pump and the substitution-fluid transfer pump; and wherein the control unit configured to control a flow rate of the dialysate transfer pump in accordance with a flow rate of the dialysate introduction pump.

2. The blood purification apparatus according to claim 1, wherein the dialysate transfer pump, the substitution-fluid transfer pump, and a drain-liquid transfer pump are each a peristaltic pump that delivers liquid by squeezing a flexible tube forming a flow route for a corresponding one of the dialysate, the substitution fluid, and drain-liquid.

3. The blood purification apparatus according to claim 1, wherein a flow rate of the dialysate introduction pump is set to a value greater than 6000 mL/h.

4. The blood purification apparatus according to claim 1, wherein a height-position difference between a bottom of the dialysate storage supported by the supporting unit and a top of the dialysate temporary chamber and a height-position difference between a bottom of the substitution-fluid storage supported by the supporting unit and a top of the substitution-fluid temporary chamber are each smaller than 40 cm.

5. The blood purification apparatus according to claim 1, wherein a height position at bottoms of the dialysate storage and the substitution-fluid storage supported by the supporting unit is lower than 160 cm.

6. The blood purification apparatus according to claim 1, wherein the supporting unit is configured such that a height position where at least one of the dialysate storage and the substitution-fluid storage is supported is adjustable.

7. The blood purification apparatus according to claim 1, wherein reaching of an amount of liquid in the dialysate temporary chamber or the substitution-fluid temporary chamber to a specified value is identified by a total amount of flow generated by the dialysate transfer pump or the substitution-fluid transfer pump.

8. The blood purification apparatus according to claim 1, further comprising:

a detecting unit that detects reaching of an amount of liquid in the dialysate temporary chamber to a specified value, wherein the control unit configured to stop the dialysate transfer pump when the reaching of the amount of liquid in the dialysate temporary chamber to the specified value is detected by the detecting unit.

9. The blood purification apparatus according to claim 1, further comprising:

a detecting unit that detects reaching of an amount of liquid in the substitution-fluid temporary chamber to a specified value, wherein the control unit configured to stop the substitution-fluid transfer pump when the reaching of the amount of liquid in the substitution-fluid temporary chamber to the specified value is detected by the detecting unit.

10. The blood purification apparatus according to claim 1, wherein the dialysate transfer pump is configured to control a flow rate of the dialysate from the dialysate storage through the first dialysate introduction line and into the dialysate temporary chamber.

11. The blood purification apparatus according to claim 1, wherein the substitution-fluid transfer pump is configured to control a flow rate of the substitution fluid from the substitution-fluid storage through the substitution line and into the substitution-fluid temporary chamber.

* * * * *